United States Patent
Reinisch

(10) Patent No.: US 9,392,943 B2
(45) Date of Patent: Jul. 19, 2016

(54) SYSTEM FOR GLYCATED PROTEIN DETECTION

(75) Inventor: Lou Reinisch, Jacksonville, AL (US)

(73) Assignee: Veritide Limited, Christchurch (NZ)

(*) Notice: Subject to any disclaimer, the term of this patent is extended or adjusted under 35 U.S.C. 154(b) by 1044 days.

(21) Appl. No.: 13/407,842

(22) Filed: Feb. 29, 2012

(65) Prior Publication Data

US 2013/0158374 A1 Jun. 20, 2013

Related U.S. Application Data

(63) Continuation of application No. 12/496,438, filed on Jul. 1, 2009, now abandoned.

(60) Provisional application No. 61/077,372, filed on Jul. 1, 2008.

(51) Int. Cl.
- *G01N 21/64* (2006.01)
- *G01N 33/68* (2006.01)
- *A61B 5/00* (2006.01)
- *C12M 1/34* (2006.01)
- *G01N 21/85* (2006.01)
- *G01N 33/48* (2006.01)

(52) U.S. Cl.
CPC ............ *A61B 5/0071* (2013.01); *C12M 1/3476* (2013.01); *G01N 21/6486* (2013.01); *G01N 21/85* (2013.01); *G01N 33/68* (2013.01); *G01N 33/6893* (2013.01); *G01N 33/48* (2013.01); *G01N 2400/00* (2013.01); *G01N 2800/042* (2013.01)

(58) Field of Classification Search
CPC ....... G01N 33/48; G01N 33/49; G01N 33/68; G01N 33/6893; G01N 21/62; G01N 21/64; G01N 21/6486; G01N 21/85; G01N 2400/00; G01N 2800/042; A61B 5/0071; C12M 1/3476
USPC .............. 436/63, 86, 87, 164, 172; 435/4, 29, 435/288.7; 422/82.05, 82.08; 600/310, 317
See application file for complete search history.

(56) References Cited

U.S. PATENT DOCUMENTS

| | | | |
|---|---|---|---|
| 7,139,598 B2* | 11/2006 | Hull ...................... | A61B 5/0059 600/310 |
| 2003/0191378 A1* | 10/2003 | Davis, III ............. | A61B 5/0059 600/310 |
| 2004/0186363 A1* | 9/2004 | Smit ..................... | A61B 5/0059 600/317 |

* cited by examiner

*Primary Examiner* — Maureen Wallenhorst
(74) *Attorney, Agent, or Firm* — Dann, Dorfman, Herrell and Skillman, P.C.

(57) ABSTRACT

A method of detecting the presence of glycated proteins or peptides (GPs) includes the steps of assessing the sample for fluorescence, subjecting the sample to UV radiation, and reassessing the sample for an increase in fluorescence. An increase in fluorescence at the reassessing step indicates the presence of GPs. The method may be useful for detecting disease such as diabetes.

20 Claims, 14 Drawing Sheets

SYSTEM FOR GLYCATED PROTEIN DETECTION

CROSS REFERENCE TO RELATED APPLICATION

This application is a continuation of U.S. application Ser. No. 12/496,438, filed Jul. 1, 2009, now abandoned, which claims the benefit of U.S. Provisional Application No. 61/077,372, filed Jul. 1, 2008, the entirety of which is incorporated herein by reference.

FIELD

The present invention relates to a system for the detection of glycated proteins or peptides (GPs).

BACKGROUND

Glycation (sometimes called non-enzymatic glycosylation) is the result of a sugar molecule, such as fructose or glucose, bonding to a protein or lipid molecule without the controlling action of an enzyme. Glycation may occur either inside the body (endogenous glycation) or outside the body (exogenous glycation). Enzyme-controlled addition of sugars to protein or lipid molecules is termed glycosylation; glycation is a haphazard process that impairs the functioning of biomolecules, whereas glycosylation occurs at defined sites on the target molecule and is required in order for the molecule to function.

Exogenous glycations may also be referred to as dietary or pre-formed. Exogenous glycations and advanced glycation endproducts (AGEs) are typically formed when sugars are cooked with proteins or fats. Temperatures over 120° C. (~248° F.) greatly accelerate the reactions, but lower temperatures with longer cooking times also promote their formation.

These compounds are absorbed by the body during digestion with about 30% efficiency. Browning reactions are evidence of pre-formed glycations. Sugar is often added to products such as french fries and baked goods to enhance browning. Until recently, it was thought that exogenous glycations and AGEs were negligible contributors to inflammation and disease states, but recent work has shown that they are important. Although most of the research work has been done with reference to diabetes, these results are most likely important for all people, as exogenous AGEs are implicated in the initiation of retinal dysfunction, cardiovascular diseases, type II diabetes, and many other age-related chronic diseases.

Food manufacturers have added AGEs to foods, especially in the last 50 years, as flavor enhancers and colorants to improve appearance. Foods with significant browning, caramelization, or with directly added preformed AGEs can be exceptionally high in these pro-inflammatory and disease initiating compounds. A very partial listing of foods with very high exogenous AGEs includes: donuts, barbecued meats, cake, and dark colored fizzy drinks.

Endogenous glycations occur mainly in the bloodstream to a small proportion of the absorbed simple sugars: glucose, fructose, and galactose. The balance of the sugar molecules is used for metabolic processes. It appears that fructose and galactose have approximately ten times the glycation activity of glucose, the primary body fuel. Glycation is the first step in the evolution of these molecules through a complex series of very slow reactions in the body known as Amadori reactions, Schiff base reactions, and Maillard reactions, all leading to advanced glycation endproducts. Some AGEs are benign, but others are more reactive than the sugars they are derived from, and are implicated in many age-related chronic diseases such as: type II diabetes mellitus (beta cell damage), cardiovascular diseases (the endothelium, fibrinogen, and collagen are damaged), Alzheimer's disease (amyloid proteins are side-products of the reactions progressing to AGEs), cancer (acrylamide and other side-products are released), peripheral neuropathy (the myelin is attacked), and other sensory losses such as deafness (due to demyelination) and blindness (mostly due to microvascular damage in the retina). This range of diseases is the result of the very basic level at which glycations interfere with molecular and cellular functioning throughout the body and the release of highly-oxidizing side-products such as hydrogen peroxide.

Glycated substances are eliminated from the body slowly, since the renal clearance factor is only about 30%. This implies that the half-life of a glycation within the body is about double the average cell life. Red blood cells are the shortest-lived cells in the body (120 days), so the half-life is about 240 days. This fact is used in monitoring blood sugar control in diabetes by monitoring the glycated hemoglobin level. As a consequence, long-lived cells (such as nerves, brain cells), long-lasting proteins (such as eye crystalline and collagen), and DNA may accumulate substantial damage over time. Metabolically-active cells such as the glomeruli in the kidneys, retina cells in the eyes, and beta cells (insulin-producing) in the pancreas are also at high risk of damage. The epithelial cells of the blood vessels are damaged directly by glycations, which are implicated in atherosclerosis, for example. Atherosclerotic plaque tends to accumulate at areas of high blood flow (such as the entrance to the coronary arteries) due to the increased presentation of sugar molecules, glycations and glycation end-products at these points. Damage by glycation results in stiffening of the collagen in the blood vessel walls, leading to high blood pressure. Glycations also cause weakening of the collagen in the blood vessel walls, which may lead to micro- or macro-aneurisms; this may cause strokes if in the brain.

The USA, New Zealand and many developed nations are facing a dangerous epidemic of type 2 diabetes. In the US, there are an estimated 20.6 million people with diabetes and 30% are undiagnosed. Another 54 million people have some form of pre-diabetes and many will develop into diabetes within three years.

Diagnosis of diabetes is typically initiated during a physical examination by a primary care physician. Screening for type 2 diabetes and pre-diabetes is inadequate. The most widely used test, the fasting plasma glucose (FPG) test, requires the subject to fast overnight before being subjected to a blood draw. The sensitivity is poor (40-60%). Currently, around 50% of patients diagnosed with diabetes already have one or more irreversible complications due to untreated diabetes.

International patent application WO 2005/045393 discloses a non-invasive method of determining a measure of glycation end-product or disease state using tissue fluorescence. A portion of the tissue of an individual is illuminated with excitation light then light emitted by the tissue due to fluorescence of certain chemicals (mainly AGEs) is detected. The detected light can be combined with a model relating fluorescence with a disease state to determine the disease state of an individual. Various correction techniques are employed to reduce determination errors due to detection of light other than that from fluorescence of a chemical in the tissue. For example, background fluorescence of the skin based on the individuals biological information can affect the measure of AGEs. This adds to the complexity of the test device.

This test device is very similar to a test device being developed by VeraLight in Albuquerque, N. Mex., USA. This uses five different excitation wavelengths of light between 350 nm and 450 nm and measures the spectrum of fluorescence from each of the five excitation wavelengths of light. The information is then analyzed with principal component analysis, with the object of separating the fluorescence of the GPs from other fluorescence in the skin, and quantifying the amount of GPs.

OBJECT OF THE INVENTION

It is an object of the present invention to provide a system for the detection of GPs which is an improvement on the above mentioned processes and/or which at least provides the public with a useful choice.

SUMMARY OF THE INVENTION

In one aspect of the invention there is provided a method of detecting the presence of glycated proteins or peptides (GPs) in a sample comprising carrying out the steps of assessing the sample for fluorescence, subjecting the sample to UV radiation, and reassessing the sample for an increase in fluorescence relative to any fluorescence assessed in said first assessing step, the presence of fluorescence at said assessing step and an increase in fluorescence at said reassessing step being indicative of the presence of GPs.

In some embodiments the physical state or phase of the sample is not altered within the steps of the method.

In one form of the invention the sample is a solid material immobilised on a support and the method includes subjecting the sample to UV radiation by irradiating the sample on the support with UV radiation and reassessment of the fluorescence of the sample.

In another alternative form the sample is a solution or a suspension, and the method includes subjecting the sample to UV radiation by subjecting the solution or suspension to UV radiation. In some embodiments the method includes measuring actual fluorescence of the sample. Additionally the method includes measuring any change in actual fluorescence between the assessment and the reassessment.

In some embodiments the fluorescence observed is spectrally resolved at the assessment and reassessment steps. Additionally the shape of the fluorescence is analysed for additional information that will give a more accurate indication of the presence of GPs.

In some embodiments the method comprises subjecting the sample between assessments to UV radiation in the wavelength range 200-320 nm, 240-320 nm, 200-300 nm, or more preferably the UV radiation wavelength is in the range 250-260 nm or about 254 nm.

The exposure time for optimal enhancement depends upon the intensity of the UV radiation source and the level of GPs that may be present in the sample. The enhancement exposure time may be less than 20 minutes, less than 10 minutes, or less than 5 minutes.

In some embodiments the method includes assessing the fluorescence of the sample, subjecting the sample to a pulse of UV radiation and reassessing the fluorescence of the sample after a delay.

In some embodiments the delay is a period of time substantially corresponding to the fluorescence lifetime of a class of GPs.

In some embodiments the steps of assessing and reassessing the fluorescence include assessing and reassessing a broadband fluorescence of the sample.

In some embodiments the steps of assessing and reassessing the fluorescence include causing the fluorescence to pass through a filter oriented to pass substantially only horizontally polarised light, and assessing and reassessing the fluorescence by reference to the horizontally polarised fluorescent light. The excitation light may be vertically polarised. Alternatively the excitation light may be unpolarised light.

In some embodiments the sample may be subjected to a modulated UV signal, and the fluorescence is reassessed for a modulated response. The reassessment may be after a period of time substantially corresponding to the fluorescence lifetime of the GP fluorescence.

In another aspect of the invention there is provided a detector for detecting GP in a sample comprising a UV source, a detection zone within which the sample may be placed or may pass, means for fluorescence analysis arranged to assess for the presence of GPs without altering the structure of any GP by assessing the sample for fluorescence, subjecting the sample to UV radiation, and then reassessing the sample for an increase in fluorescence relative to any fluorescence assessed in said first assessing step, the presence of fluorescence at said assessing step and an increase in fluorescence at said reassessing step being indicative of the presence of GPs.

In some embodiments the output of the detector is actual fluorescence measurements of the two assessments.

Alternatively or additionally the output of the detector may comprise a reading indicative of the change in fluorescence between the two assessments.

In some embodiments the detector is arranged to assess and reassess the fluorescence of the sample by reference to substantially only horizontally polarised fluorescence light. The excitation light may be vertically polarised. Alternatively the excitation light may be horizontally polarised.

In some embodiments the detector is arranged to subject the sample between assessments to UV radiation in the wavelength range 200-320 nm, 240-320 nm, 200-300 nm, or more preferably the UV radiation wavelength is in the range 250-260 nm or about 254 nm.

In some embodiments the detector is arranged to spectrally resolve the fluorescence observed at the assessment and reassessment steps. Additionally the detector may analyse the shape of the fluorescence for additional information that may give a more accurate indication of the presence of GPs.

In some embodiments the detector is arranged to assess and reassess broadband fluorescence of the sample.

In some embodiments the detector is arranged to reassess the fluorescence of the sample after a delay of 0.1-10 ns and more preferably the delay is a period of time that corresponds to the fluorescence lifetime of the GP fluorescence.

In some embodiments the sample may be subjected to a modulated UV signal, and the fluorescence is reassessed for a modulated response. Preferably the reassessment is after a period of time substantially corresponding to the fluorescence lifetime of the GP fluorescence.

In another aspect of the invention there is provided a method ascertaining whether a sample being a portion of skin of an individual, due to its content of GPs, indicates the presence of a disease in the individual comprising the steps of providing a detector which comprises UV source, a detection zone within which a sample may be placed or may pass, means for fluorescence analysis arranged to assess for the presence of GPs by reference to a first assessment of the sample for fluorescence, exposure of the sample to the UV source, and a reassessment of the sample for an increase in fluorescence relative to any fluorescence assessed in said first assessing step, the presence of fluorescence at said first assessment step and an increase in fluorescence at said reassessment step being indicative of the presence of GPs, all without altering the structure of any GP; setting the sensitivity of the detector at a predetermined threshold above which a disease would be considered to be present, positioning the detector so that the sample is in the detection zone, and reading or interpreting the output of the detector as either a. above the threshold and thus indicative of the presence of disease, or b. below the threshold and thus not indicative of the presence of disease.

In some embodiments the physical state of the sample being a portion of skin of an individual is not altered within the steps of the method.

In some embodiments the detector is adapted to detect and identify diabetes.

In another aspect of the invention there is provided a method of detecting the presence of GPs in a sample comprising carrying out the steps of assessing the sample for fluorescence, subjecting the sample to UV radiation, then reassessing the sample for fluorescence, and spectrally resolving fluorescence observed in the assessment and reassessment steps and analysing the spectrally resolved fluorescence for an increase in fluorescence indicative of the presence of GPs.

In a final aspect of the invention there is provided a detector for detecting GPs in a sample comprising a UV source, a detection zone within which the sample may be placed or may pass, means for fluorescence analysis arranged to assess for the presence of GPs without altering the structure of any GP by assessing the sample for fluorescence, subjecting the sample to UV radiation, then reassessing the sample for fluorescence, spectrally resolving fluorescence observed in the assessment and reassessment steps, and analysing the spectrally resolved fluorescence for an increase in fluorescence indicative of the presence of GPs.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DEFINITIONS

As used herein the following terms have the meanings given:

"fluorescence" means the emission of light of a longer wavelength by a source caused by exposure to light of a shorter wavelength from an external source.

"fluorescence lifetime" refers to how long the fluorescence process exists after the sample is excited.

"sample" means any sample of whatever form including particulate, powders such as for example milk or whey powder, on a surface static or moving or airborne, in solution or suspension including cloudy liquids such as milk, and includes a portion of skin or a blood sample of a person or animal or a derivative from blood, a sample such as a urine, lymph, faeces, or hair sample, or a tissue sample including but not limited to a biopsy of an artery or organ from a person or animal.

"vertically polarised" and "horizontally polarised" in relation to light are used with respect to the scattering plane or surface. In the cases of the samples under investigation, the surface may be the surface of the molecule, or a solid phase; it is relative to the direction of the light and of the species which is responsible for light reflection and/or absorption.

"and/or" means "and" or "or", or both.

As used herein "(s)" following a noun means the plural and/or singular forms of the noun.

The term "comprising" as used in this specification and claims means "consisting at least in part of", that is to say when interpreting independent paragraphs including that term, the features prefaced by that term in each paragraph will need to be present but other features can also be present.

BRIEF DESCRIPTION OF THE DRAWINGS

The invention will now be described by way of example only and with reference to the drawings in which.

DETAILED DESCRIPTION OF THE INVENTION

We have found that GPs will exhibit fluorescence enhancement on UV exposure. The invention comprises:

assessing the fluorescence of a sample (such as but not limited to a portion of skin of an individual) which is suspected of containing GPs, exposing the sample to ultraviolet radiation, reassessing the fluorescence of the sample, and determining the presence (or absence) of GPs.

Figure 1:
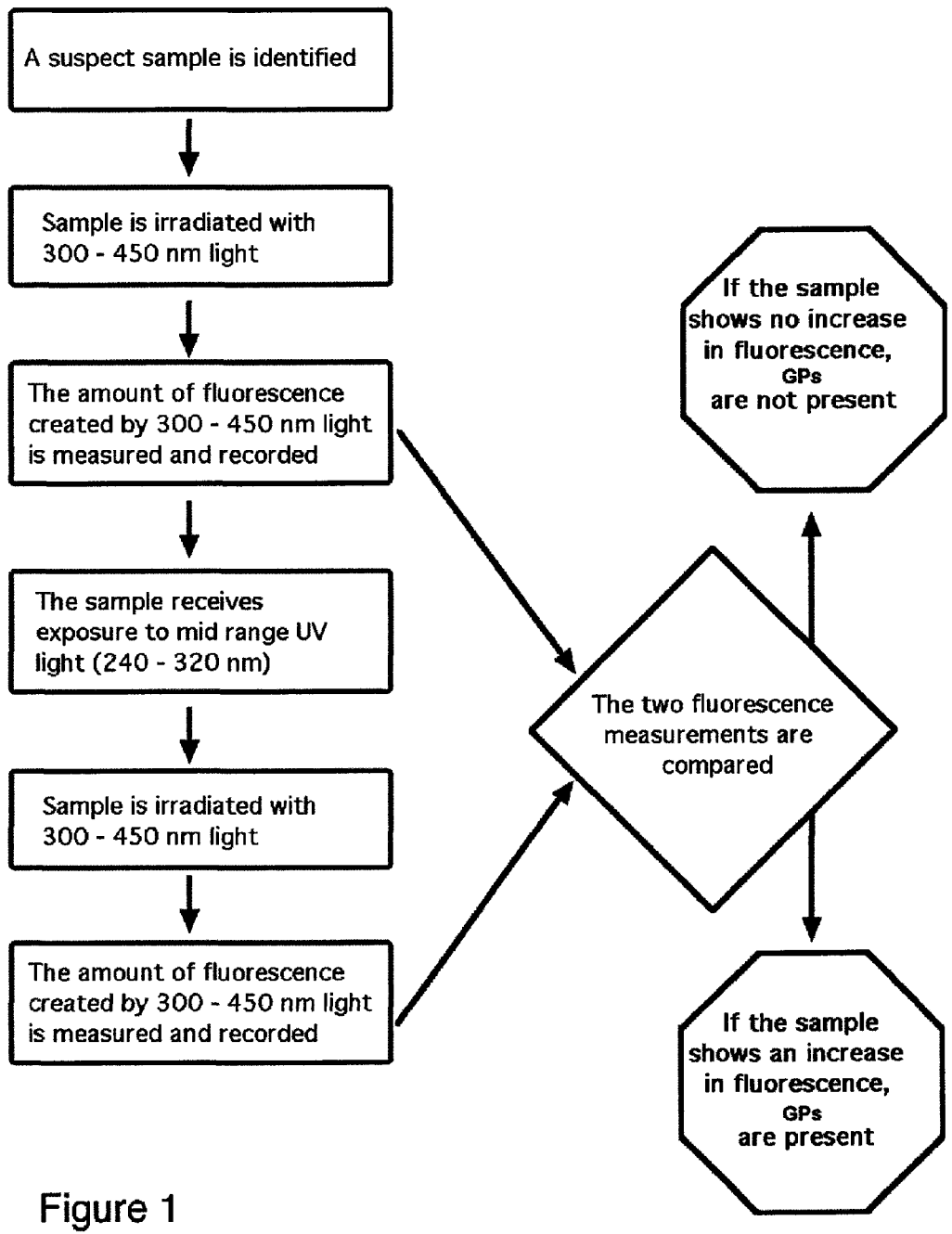
FIG. 1: is a generalised flow diagram of the method of the invention.

If the fluorescence is increased after exposure to UV radiation the sample is assessed as containing GPs. The method is illustrated generally in the flow diagram of FIG. 1 (in which the wavelength ranges are given by way of example).

Figure 2:
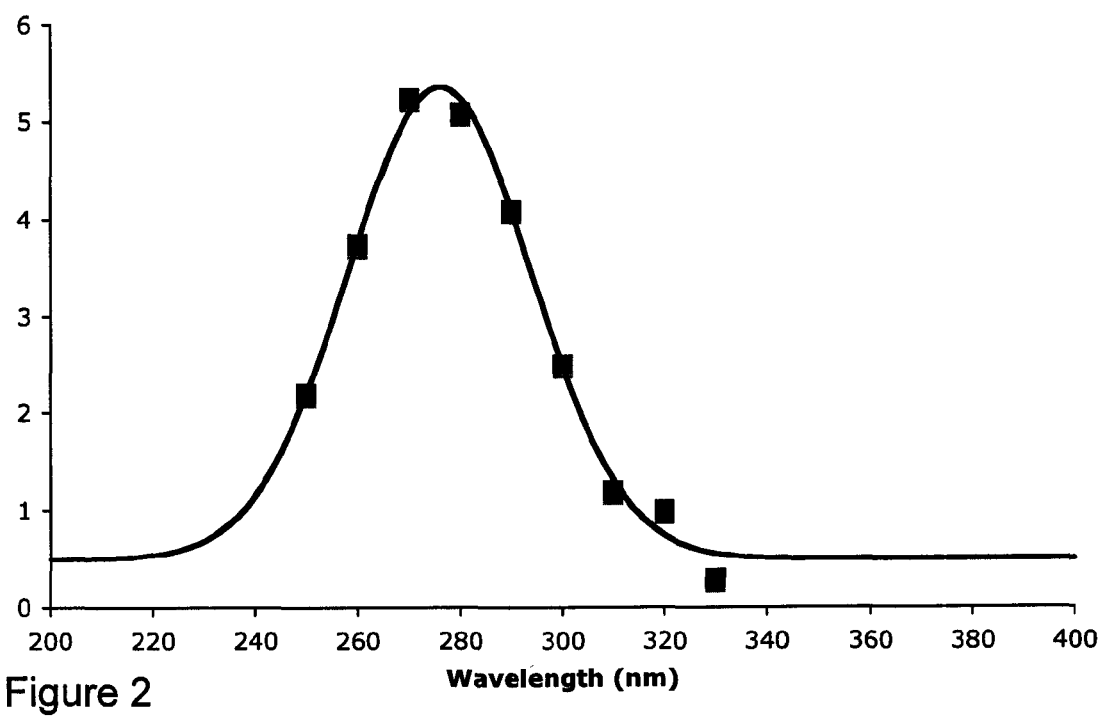
FIG. 2: is a plot of the spectral response for the enhancement of GP fluorescence.

FIG. 2 shows the spectral response curve for the enhancement of the GP fluorescence. The full range of enhancement runs from about 230 nm to 330 nm. However the peak enhancement occurs on exposure to UV light of about 254 nm. The squares show measured intensities. The line is a least squares fit of a Gaussian profile to the measured data. As the maximum enhancement is observed at or near 254 nm this is an ideal region of the spectrum for assessing fluorescence enhancement.

In the assessment and reassessment of fluorescence the sample may for example be exposed to UV in the wavelength range 200-300 nm or 300-450 nm and the fluorescence detected in the wavelength range 300-600 nm or 300-450 nm. The fluorescence may be integrated over the wavelength range of each fluorescence assessment and the integrated results compared for a fluorescence increase, or increase beyond a difference threshold, as indicative of the presence of GPs.

Optionally the fluorescence information from the detector(s) may be corrected to reduce errors, due to detection of light other than from fluorescence of glycated proteins or peptides for example. The background fluorescence may be subtracted, and also optionally the fluorescence information may be adjusted to compensate for the colour of the skin of the subject by for example dividing all the values of the detected spectrum by the values between 350-400 nm, to produce a normalised spectrum.

Figure 3:
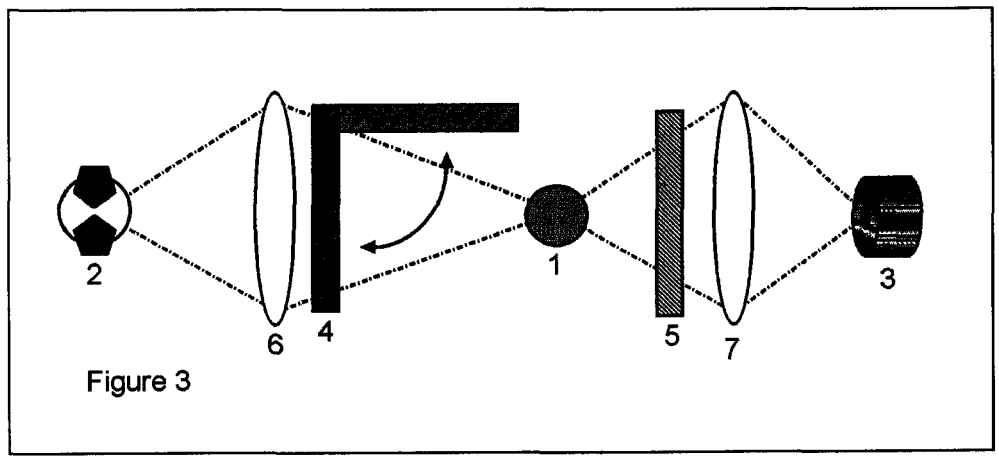
FIG. 3: is a schematic of an embodiment of a detector in accordance with the invention.

FIG. 3 schematically illustrates the functional elements one embodiment of a detector (and method) in accordance with the invention. The Figure schematically illustrates the sample 1, and detector elements being a broad band UV lamp 2 as the UV source, and a diode detector 3. The UV radiation is focussed onto the sample by means of a lens 6, and the light passes through a long wavelength UV filter 4 (such as a 350 nm filter). The fluorescence passes through a further filter 5 (such as a 450 nm filter) to block the light that is simply reflected from the sample and to make certain that only the fluorescence will be detected, before being focused by means of a lens 7, and detected by the detector 3. The amount of light detected for the purposes of this discussion will be called measurement #1. The long wavelength UV filter 4 is then be rotated out of the optical path and the sample is irradiated with all wavelengths of light from the lamp, including the short and mid wavelength UV light. The detector is not used during this time. Finally, the long wavelength UV filter 4 is rotated back into the optical path. The fluorescence passes through filter 5 and lens 7 to detector 3. If the intensity of the fluorescence at detector 3 has increased over measurement #1, or increased beyond a threshold margin over the fluorescence intensity of measurement #1, the sample may contain GPs. The amount of increase may be proportional to the amount of GPs.

Figure 4:
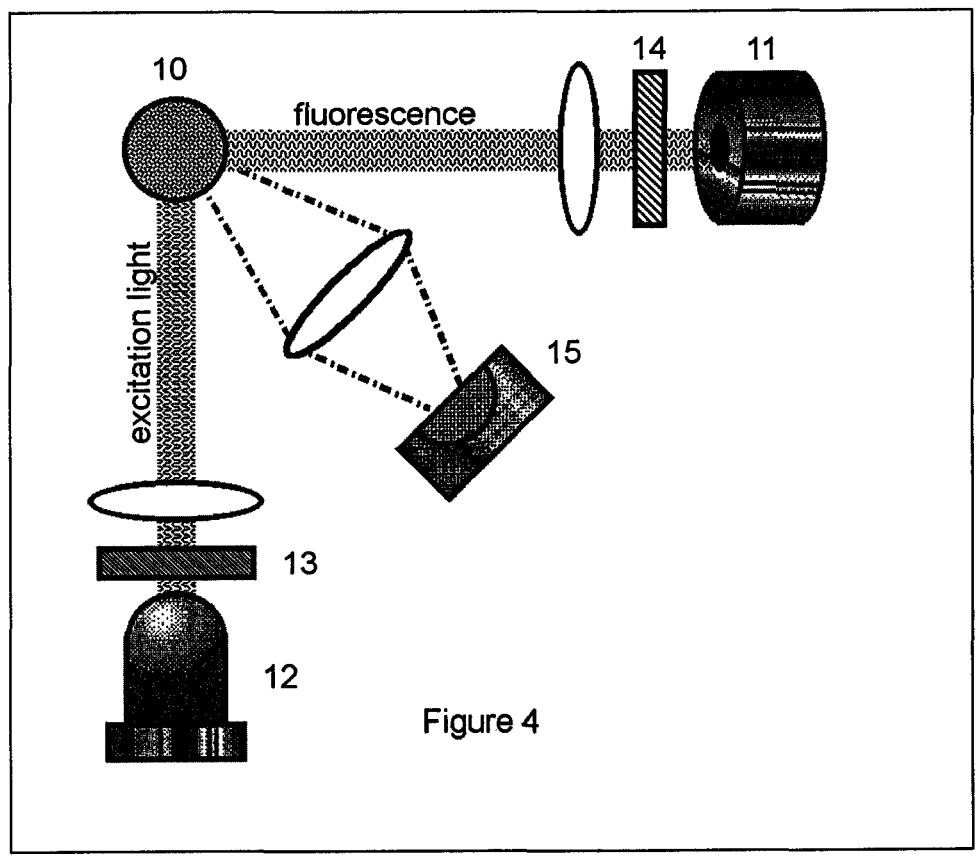
FIG. 4: is a schematic of an alternative embodiment of a detector in accordance with the invention.

FIG. 4 schematically illustrates the functional elements of another embodiment of a detector (and method) of the invention, that comprises no moving parts (like the rotating filter used in FIG. 2). The Figure illustrates the sample 10, a UV lamp 12, which may be a UV light emitting diode or a diode laser as the UV source, and a diode detector 11. The UV radiation can pass through a long wavelength UV filter 13 (such as a 350 nm filter) if the light from UV source is broadband. If a UV light emitting diode or UV diode laser is used the filter may not be necessary. The light might be further focussed on the sample with a lens. The fluorescence can be collected by a second lens, and passes through a filter 14 (such as a 450 nm filter) to block light simply reflected from the sample so that only the fluorescence is detected by the detector 11. The sample is irradiated with a second UV lamp 15, emitting 250 to 300 nm UV light. This lamp may not need to be filtered, and can be focussed onto the sample by a lens. The detector 11 is not used during this time. Finally, the sample is again irradiated with the UV lamp 12 and the fluorescence is collected by a lens and passes through the filter 14 to detector 11. If the intensity of the fluorescence at detector 11 at the second measurement has increased over the first, or increased beyond a threshold margin over the fluorescence intensity of the first measurement, then the sample may contain GPs. The amount of increase may be proportional to the amount of GPs.

Figure 5:
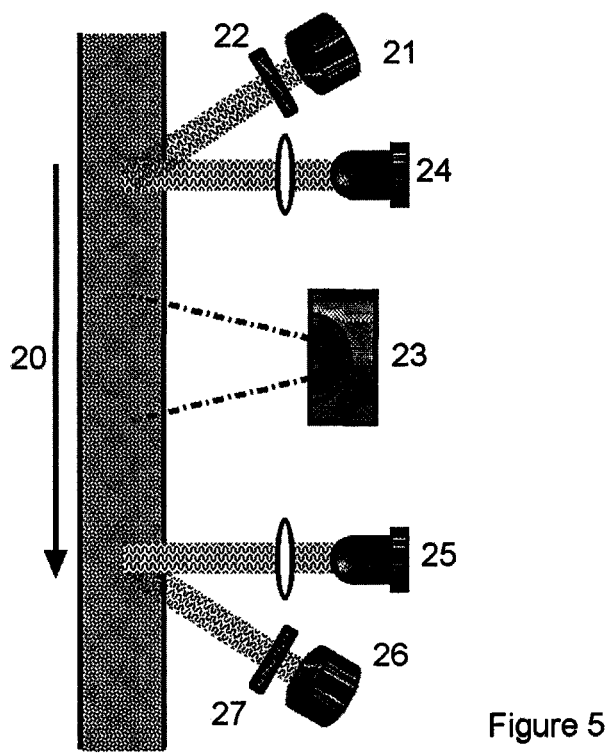
FIG. 5: is a schematic of an alternative embodiment of a detector in accordance with the invention.

FIG. 5 schematically illustrates a further embodiment of a detector (and method) of the invention in which the sample is moving, such as milk powder moving on a conveyer belt. The Figure illustrates the sample 20, moving at a constant speed as shown by the arrow, a UV lamp 24, which may be a UV light emitting diode or a diode laser as the UV source, and a diode detector 21. The UV radiation can pass through a long wavelength UV filter—not shown (such as a 350 nm filter) if the light from UV source is broadband. If a UV light emitting diode or UV diode laser is a used a filter may not be necessary. The light may be further focussed on the sample with a lens. The fluorescence can be collected by a second lens (not shown), and passes through a filter 22 (such as a 450 nm filter) to block light simply reflected from the sample, to detector 21. The sample is then irradiated by a second UV lamp 23, with 250 to 300 nm UV light. This lamp does not need to be filtered, but can be focussed onto the sample (no lens shown). Finally, the sample is again irradiated with the UV lamp 25, which might be a UV light emitting diode or a diode laser as the UV source, and a diode detector 26. The UV radiation can pass through a long wavelength UV filter—not shown (such as a 350 nm filter) if the light from UV source is broadband. If a UV light emitting diode or UV diode laser is a used the filter will not be necessary. The light might be further focussed on the sample with a lens. The fluorescence can be collected by a second lens (not shown), and passes through a filter 27 (such as a 450 nm filter) to block reflected light, to the detector 26. If the intensity of the fluorescence at detector 26 has increased, or increased beyond a threshold margin over the fluorescence intensity of the first measurement, then the sample may contain GPs. The measurements between detectors 21 and 26 must be delayed by the time required for the sample to move between the two detectors.

UV light sources include lamps (including fluorescent lamps, gas lamps, tungsten filament lamps, quartz lamps, halogen lamps, arc lamps, and pulsed discharge lamps, for example), and UV light emitting diodes, laser diodes, laser of any type capable of producing UV radiation (such as gas, dye or solid state) and two-photon techniques where two separate photons of differing wavelength as used to provide the required excitation wavelength. For example, a 254 nm light to bring about fluorescence enhancement can be achieved from a high intensity of 508 nm light. Two photons of 508 nm could be simultaneously absorbed to create the same effect and response as one 254 nm photon being absorbed. An advantage of such a two-photon absorption is that all optics and the light emitter work in the visible region of the spectrum, whilst the absorption band of the sample is in the UV region. When subjecting the sample to UV radiation is referred to, scenarios such as this are included. It is the absorption band which should be considered in this case.

Other than with the two-photon method, the bandwidth of the exciting light does not have to be very narrow. Thus some of the light sources discussed above may not need filtering, or could simply be filtered by gratings, interference fitters, coloured glass filters, or cut-off filters.

The detector may be any photodetector for the detection of light, including, but not limited to, photodiodes, phototransisitors, photoresistors, photomultipliers, pyroelectric detectors, and chemical detectors, such as photographic plates. The detector can be a single element detector such as a photodiode that measures all light incident on the detector window, or an image detector, such as a silver halide emulsion on a photographic plate or a CCD photodiode array. The detector needs to be sensitive to the range of wavelengths of light emitted from the fluorescing GPs.

A detection system of the invention may include means for analysis of the fluorescence, such as a computer processing apparatus which, for example records fluorescence recorded or detected before irradiation and compares it with that recorded or detected after, and identifies any fluorescence enhancement indicating the presence of GPs. The analysis means may determine actual fluorescence measurements or may simply determine the difference between the first and subsequent recording, and determine if an enhancement has been observed. The analysis means may record and store the outputs or it may simply trigger a light for example, if GPs (or GPs content greater than a threshold limit) are detected.

Optionally polarised light may be used to improve the ratio of the fluorescence signal to the background signal. If the irradiating UV light is polarised, although the scattered (background) radiation will preserve the polarisation of this light, the fluorescence signal does not. Thus if the sample is irradiated with vertically polarised light, although the scattered light will remain vertically polarised, that light which is fluoresced from the sample (as a result of the presence of GPs) is a mixture of horizontally polarised and vertically polarised radiation. By measurement of only the horizontally polarised light, fluorescence is measured with little, if any, background scattering. Alternatively the excitation light may be unpolarised light, and only the horizontally polarised fluorescent light is measured.

Figure 6:
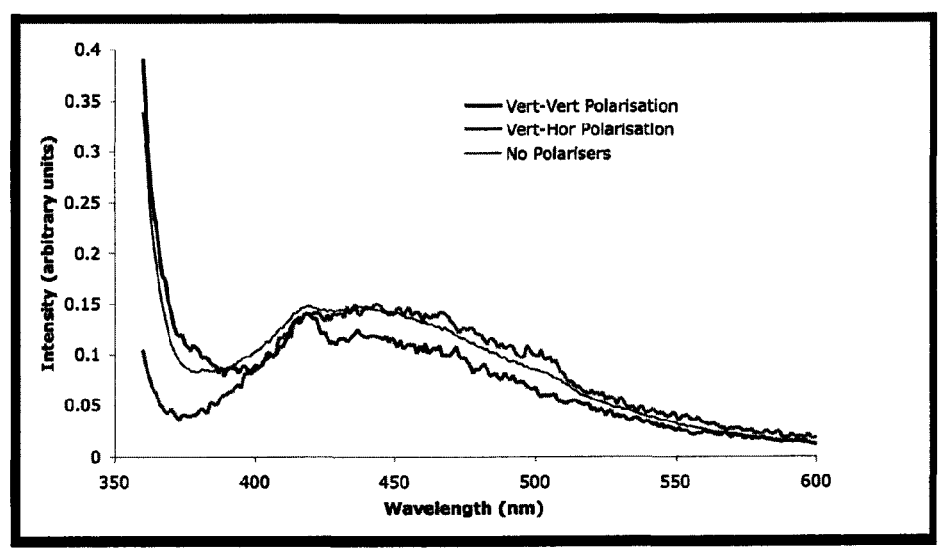
FIG. 6: is plot of fluorescence intensity against emission wavelength showing the effect of using polarised light on the signal to noise ratio.

The terms "vertical" and "horizontal" polarisation are used with reference to the "scattering surface". In the preferred form of this embodiment of the invention we use the 90 degree geometry between incident and scattered light, and the incident radiation is polarised vertically (with respect to the scattering surface or phase). The scattering surface or phase will depend upon the nature of the sample being investigated but is the molecule or species responsible for reflecting and/or absorbing the incident light. FIG. 6 is a plot of intensity against wavelength showing fluorescence from GPs observed for the arrangements of no polarisation; vertical-vertical polarisation (ie vertical incoming light; vertical detected fluorescence) and vertical—horizontal ((ie vertical incoming light; horizontal detected fluorescence). This shows an improvement of signal to noise for the vertical-horizontal arrangement as discussed previously. This is particularly true at the lower wavelengths.

Polarising filters may be incorporated into the previously described embodiments, such as at least a horizontally polarising filter before the detector, and a vertically polarising filter may also be employed with the UV source.

The wavelengths of fluorescence may be different depending upon the materials present in the sample. Thus in a preferred embodiment, a more specialised detector resolves the intensity of emission as a function of wavelength, the shape of the fluorescence can be analysed to determine a more accurate indication of the presence and amount of GPs in a sample.

Some embodiments of the invention may take advantage of the phenomenon that fluorescence has a distinct lifetime. This lifetime is relative to that of the scattered light, which has a zero lifetime. Specifically, after light is absorbed by the GP it takes a short amount of time for the fluorescence to occur. This is usually between 0.1-10 ns. Thus in general terms if following a short pulsed excitation, emitted light having a zero lifetime is ignored and other emitted light detected, the contribution to the emission by scattering is reduced and thus the signal to noise ratio improved.

An alternative means of taking advantage of this phenomenon involves modulating the intensity of the light, for example in a sinusoidal fashion. The fluorescence of the GP follows the modulation of the exciting light, delayed by the fluorescence lifetime of the enhanced GP. Thus in this embodiment a modulated fluorescence signal is detected (again for example a sine wave type signal, if the exciting light was modulated accordingly) delayed by the fluorescence lifetime.

The invention provides a method for detection of GPs (which can be carried out non-invasively for human subjects). Thus the method may be implemented, for example on a handheld detector.

The invention has importance in the detection of disease however there are many other applications as would be known to one skilled in the art.

In the field of disease detection the invention may be useful for detecting diabetes or a propensity towards diabetes in a living person or an animal and in particular type II diabetes, or other diseases such as retinal dysfunction, or cardiovascular disease (including but not limited to atherosclerosis, arteriosclerosis or arteriolosclerosis), obesity, metabolic syndrome, neurodegenerative disease, cancer, or renal disease, for example. The method of the invention may be carried out in such applications by non-invasively fluorescence—UV exposure-fluorescence reassessment of the skin of a living person, or of a blood sample from the person. A detector arranged to carry out the method of the invention may be implemented as a relatively small diagnostic instrument such as a table-top diagnostic instrument for example, on a bed of which a person places, or into which a person inserts, his or her hand or forearm for fluorescence enhancement analysis of the invention, or as a handheld diagnostic instrument, for example. The presence of a GP in a sample from a person is indicative of the presence of a disease such as those listed above. In particular, the presence of fluorescence at said assessing step and an increase in fluorescence at said reassessing step is indicative of the presence of a GP in a sample from a person, and therefore the presence of a disease in the person.

Figure 13:
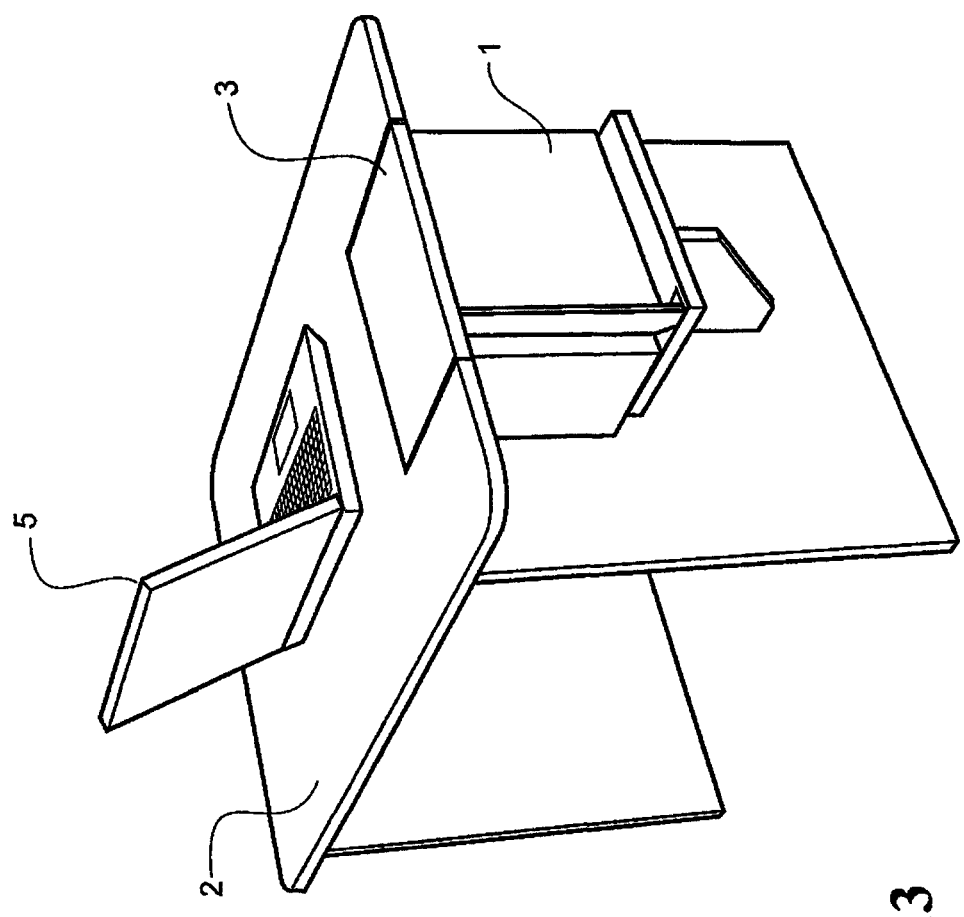
FIGS. 13 and 14: show an embodiment of a detector of the invention incorporated in a desk.
Figure 14:
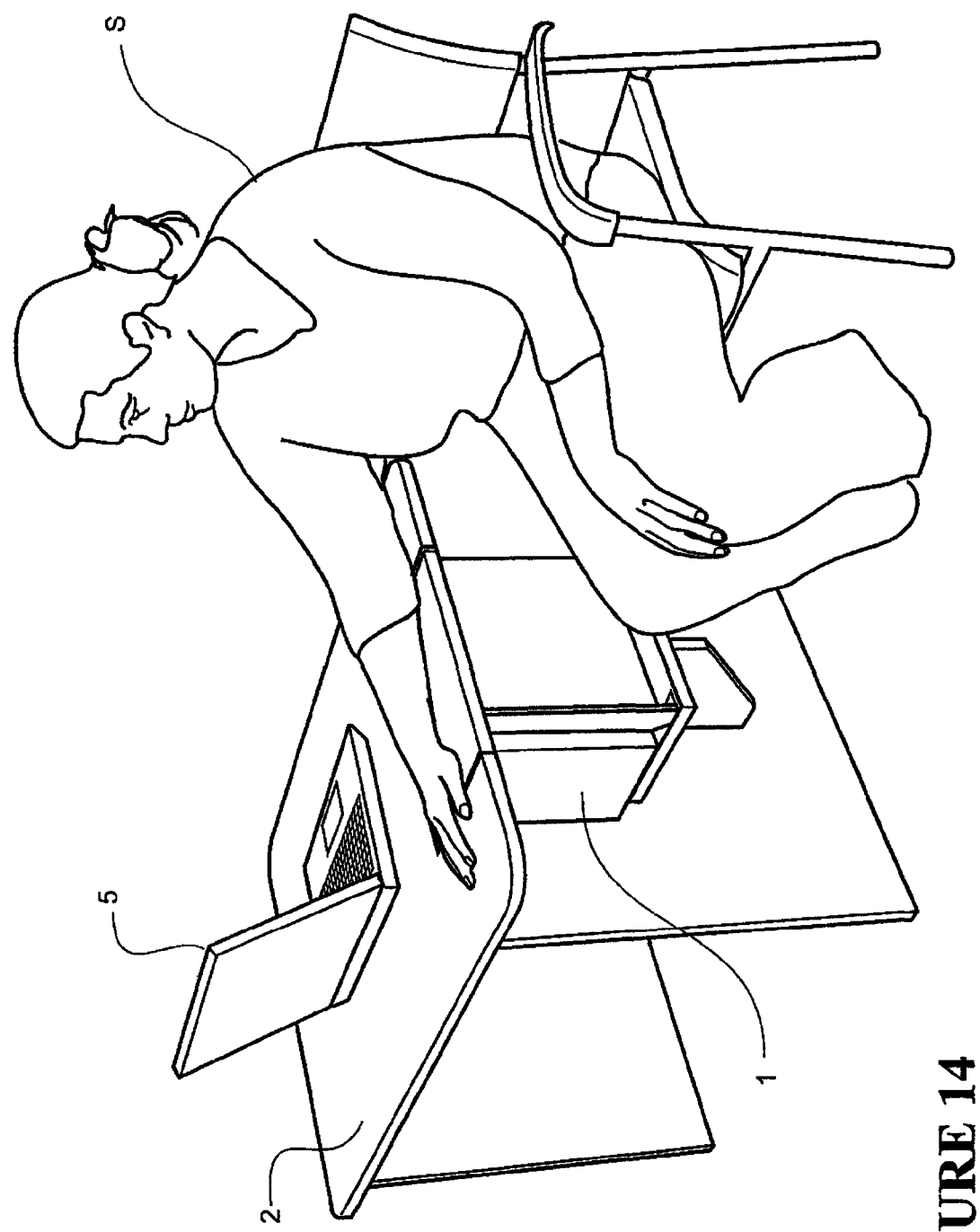

FIGS. 13 and 14 show an embodiment of a detector of the invention incorporated in a desk. A module 1 is mounted to the side of a desk 2. The top surface of the desk comprises one or more optical apertures 3 from within the module 1. Within the module 1 are housed optical components of the detector such as one or more light sources such as lasers, one or more detectors, and electronics such as a computer processor and memory. Alternatively data from the detectors may be supplied to external computer processing apparatus such as a personal computer 5 connected to the module 1. In use a subject indicated at S in FIG. 14 places his or her forearm on the desktop over the optical aperture(s) 3, before operation of the detector as described above as initiated.

Figure 15:
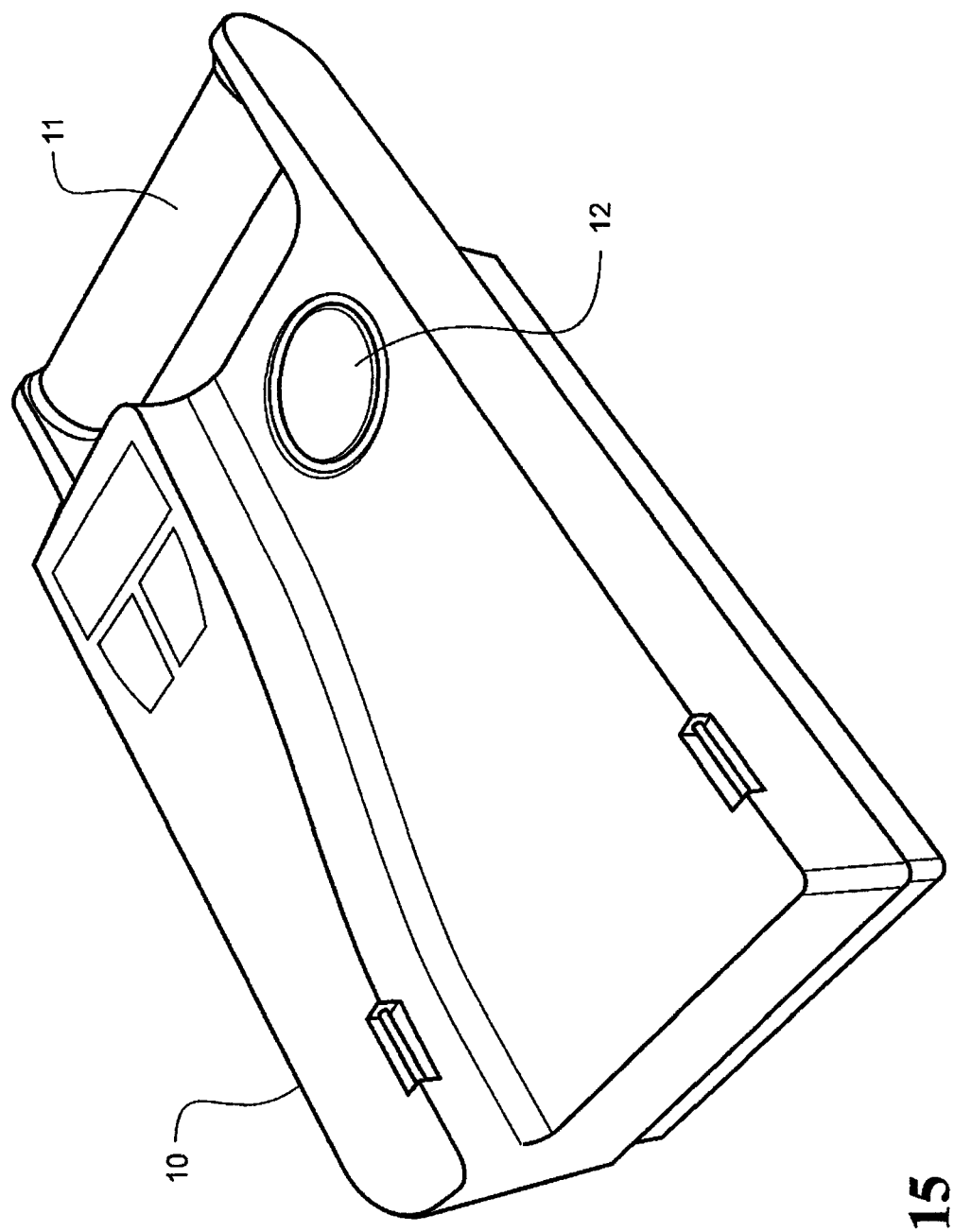
FIG. 15: shows an embodiment of a portable desktop detector of the invention.

FIG. 15 shows an embodiment of a portable desktop detector of the invention. The desk top instrument 10 comprises a hollow casing, moulded from a plastics material for example, within which are housed optical components of the detector such as one or more light sources such as lasers, one or more detectors, electronics such as a computer processor and memory, and a power source typically a battery although the unit may also or alternatively comprise a power cord or socket for connection to an external power supply such as mains power or an external battery. The instrument is of a size that it can be conveniently carried by an individual and includes a carry handle 11. The instrument may be placed on a table top or desktop for example, for use. An optical aperture 12 is provided in the top surface of the casing through which the laser(s) and detector(s) of the instrument may operate. The top surface of the instrument may be shaped as at 13 to position the forearm of a subject on the instrument over the optical aperture 12 for use.

It is also worthy of note that it may be possible to detect single GPs. For example it is common to frequency double, triple and quadruple the light from a Nd:YAG laser. With use of the tripled (355 nm) and the quadrupled (266 nm) light from a Nd:YAG laser, the resolution is such that single GPs may be detected by the method of the invention. Lasers other than the Nd:YAG could also be used, such as diode lasers.

The following description of trials work further illustrates the invention.

Trial 1
Method

It is known that the level of glycated haemoglobin correlates very well with diabetes. A normal patient will have a level of glycated haemoglobin between 4.0 and 6.0%. A diabetic patient will have a glycated haemoglobin level above 6.9%. It is assumed that the level of GPs in the skin (glycated collagen) will correlate with the levels of glycated haemoglobin, and that measuring the amount of glycated collagen in skin is a screening tool for diabetes.

Figure 7:
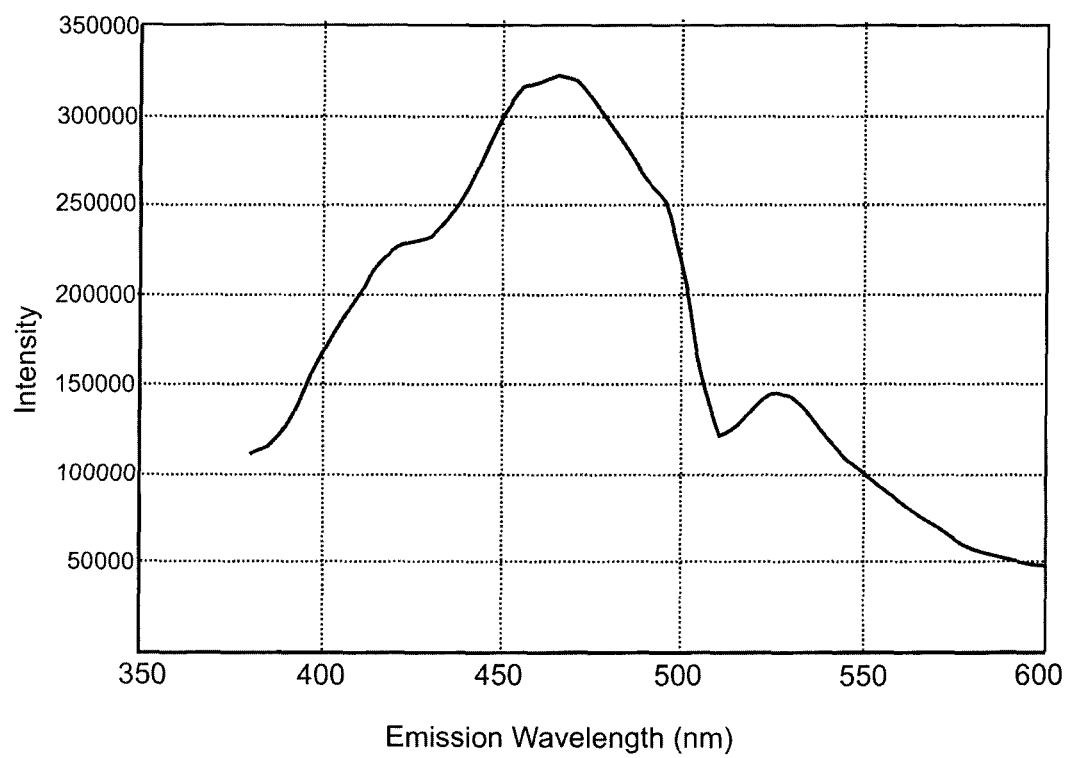
FIG. 7: is a plot of intensity against wavelength for the fluorescence of a human forearm as discussed in Trial 1 subsequently described.

A portion of skin of each of the subjects referred to below was exposed to a single excitation wavelength of 350 nm, and emission wavelengths from 380 to 600 nm were measured. Enhancement was generally performed with a 5 W germicidal lamp emitting 254 nm wavelength light, next to the skin for 60 seconds, in some cases and 10 seconds in others. The skin portion was again exposed to the same excitation wavelength and fluorescence reassessed. FIG. 7 shows the typical fluorescence spectrum of skin, the excitation wavelength was 350 nm and the intensity was measured in arbitrary units.

Results

Figure 8:
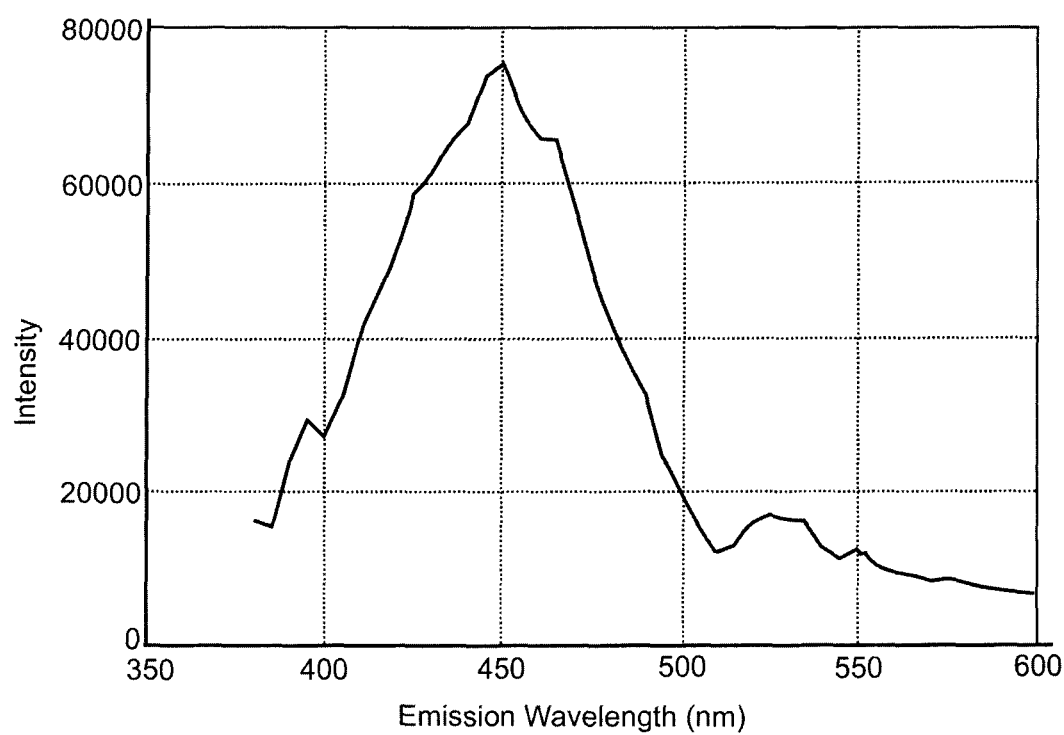
FIG. 8: is a plot of intensity against wavelength for the fluorescence difference before and after irradiation with UV radiation of a diabetic subject as discussed in Trial 1.

FIG. 8 shows the difference spectrum (the spectrum after exposure to 254 nm UV light for 60 seconds minus the spectrum before exposure to 254 nm light) of a known type II diabetic subject. The intensity scale is arbitrary. The relative intensity is near 80,000 at the peak.

Figure 9:
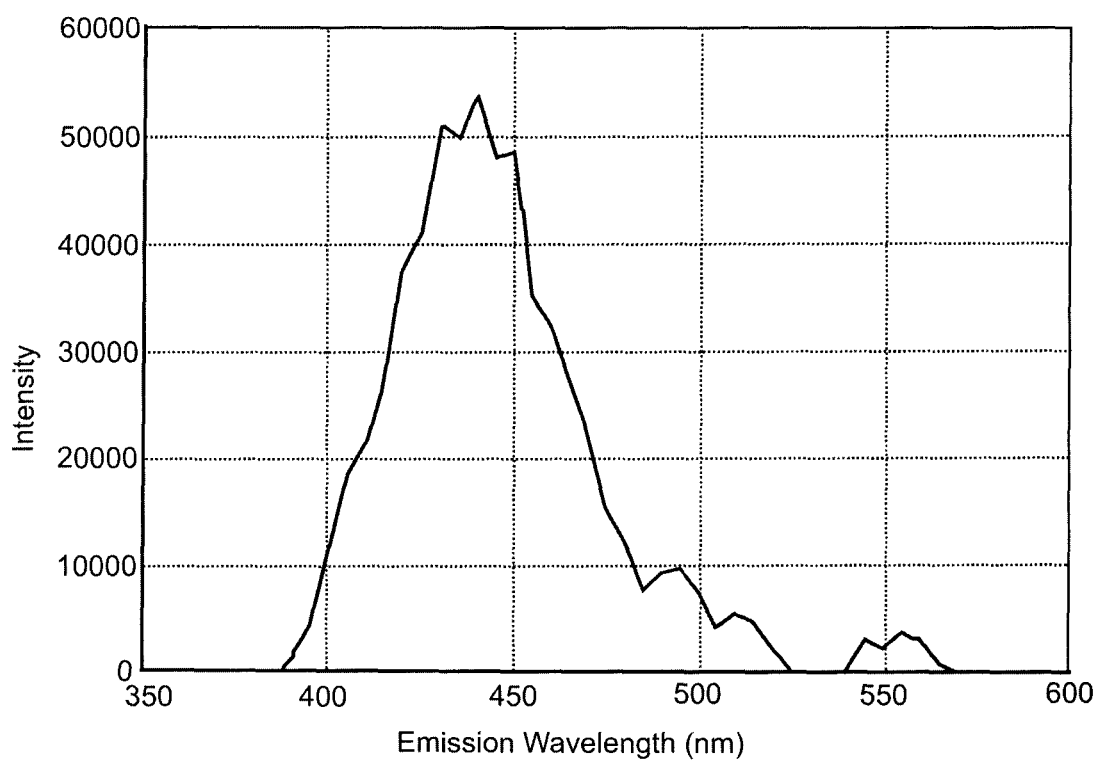
FIG. 9: is a plot of intensity against wavelength for the fluorescence difference spectrum of a subject where there is a family history of diabetes as discussed in Trial 1.

FIG. 9 shows the difference spectrum (the spectrum after exposure to 254 nm UV light for 60 seconds minus the spectrum before exposure to 254 nm light) of a 53 year old subject where both parents are diabetic. The intensity scale is arbitrary. The relative intensity is near 50,000 at the peak.

Figure 10:
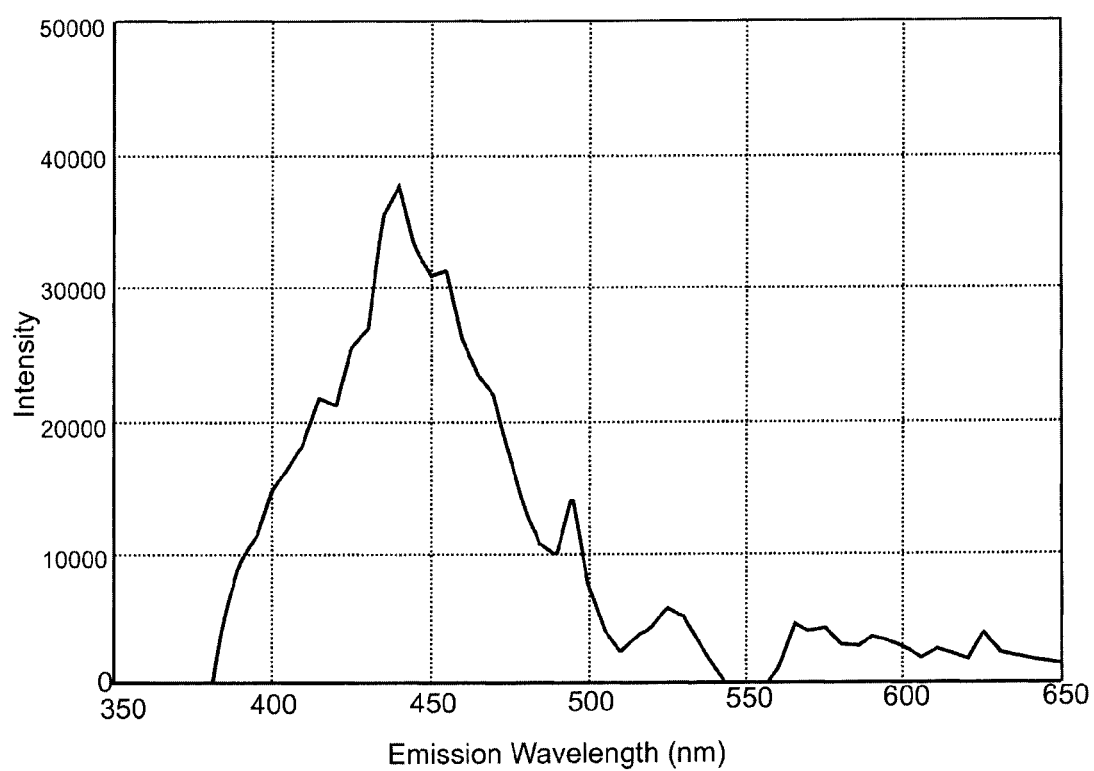
FIG. 10: is a plot of intensity against wavelength for the fluorescence difference spectrum of a 22 year old female with no history of diabetes as discussed in Trial 1.

FIG. 10 shows the difference spectrum of a young 22 year old woman with no history of diabetes. The intensity of the peak is near 40,000. This is significantly lower than the peak of nearly 80,000 measured for the diabetic subject (FIG. 8).

Figure 11:
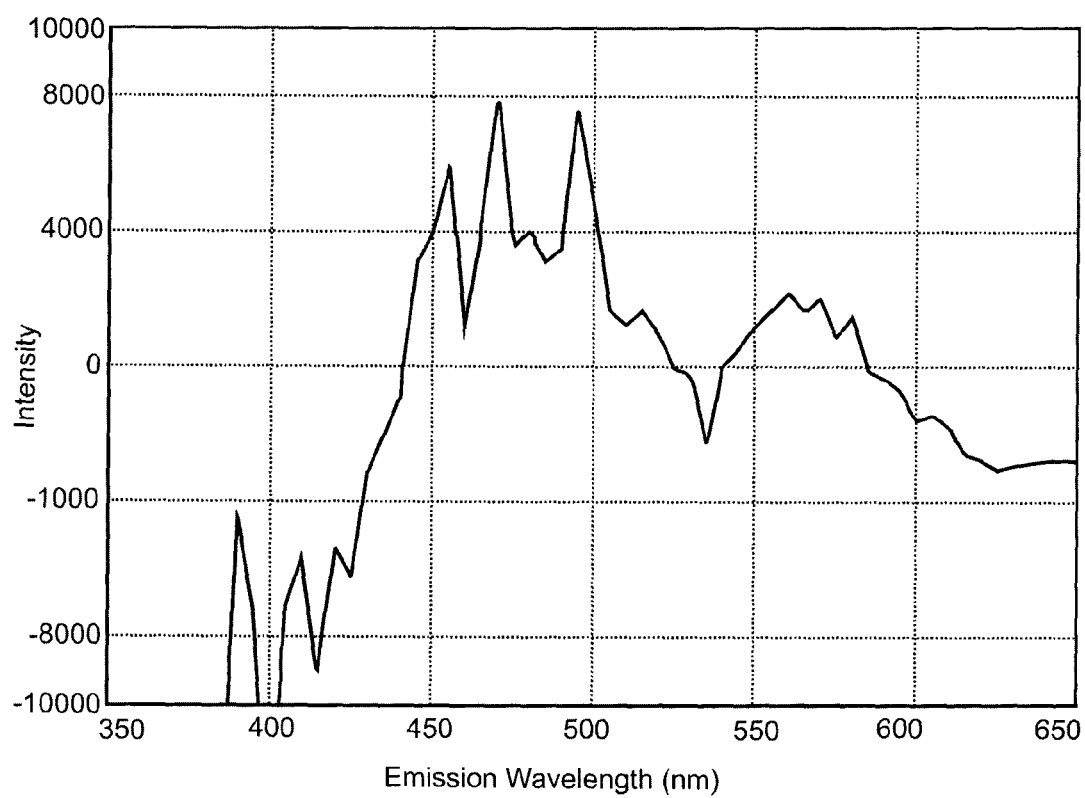
FIG. 11: is a plot of intensity against wavelength for the fluorescence difference spectrum of a 23 year old male with no history of diabetes as discussed in Trial 1.

FIG. 11 shows the difference spectrum of a 23 year old male with no history of diabetes. The spectrum appears very noisy. This is because the peak is only near 4000. This is significantly lower than the peak of nearly 80,000 measured for the diabetic subject (FIG. 8).

Trial 2
Method

During a 10 week period clinical data and enhanced skin autofluorescence (ESAF) measurements were obtained from 33 live persons with diabetes and 19 healthy, non-diabetic persons as controls. ESAF was measured in quadruplicate on the subjects' forearms and hands using a computer-controlled fluorospectroscope. Initially, variable UV exposure times were used, and in the latter part of the study the UV exposure time between fluorescence measurement and reassessment was 10 seconds.

Results

Figure 12:
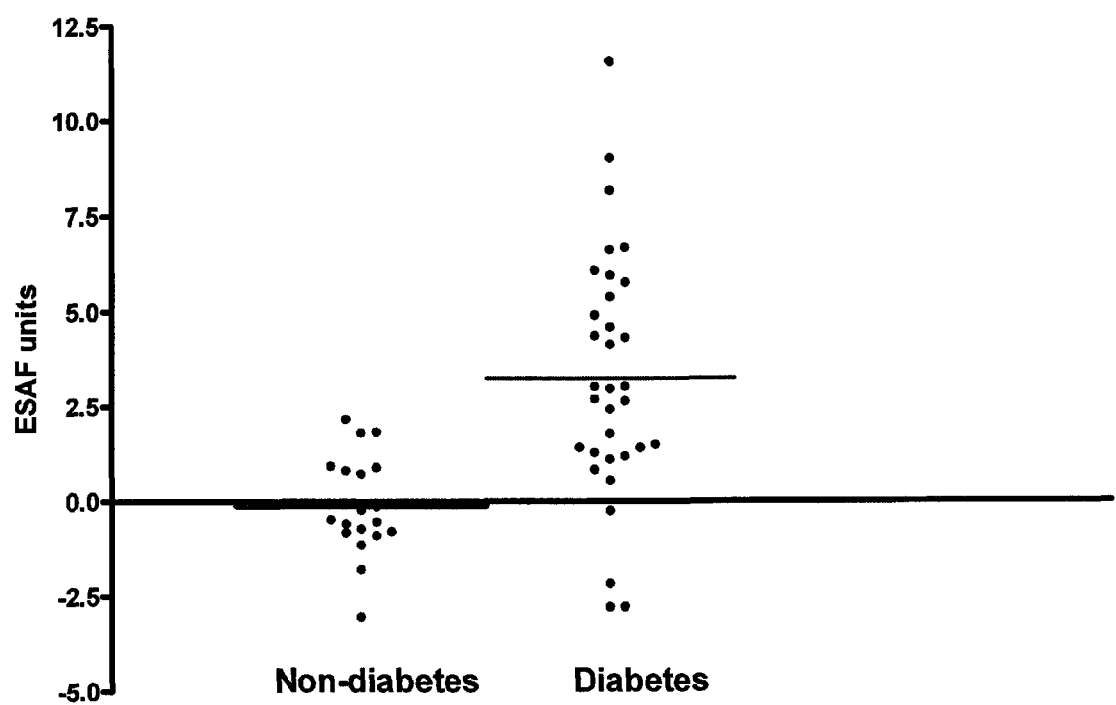
FIG. 12: is a scattergraph of fluorescence enhanced results for non-diabetic and diabetic groups, referred to in the subsequently described Trial 2.

The mean ESAF results were approximately 30-fold higher in the diabetic group compared to the controls. FIG. 12 is a scatter graph comparing the ESAF measurements in the diabetic and control groups, and shows the significantly higher readings in the patients with diabetes.

The invention claimed is:

1. A method of detecting the presence of glycated proteins or peptides in a sample comprising carrying out steps of first assessing the sample for fluorescence, subjecting the sample to UV radiation, and reassessing the sample for an increase in fluorescence relative to any fluorescence assessed in said first assessing step, the presence of fluorescence at said first assessing step and an increase in fluorescence at said reassessing step being indicative of the presence of glycated proteins or peptides.

2. A method according to claim 1 including subjecting the sample between assessments to UV radiation in a wavelength range 200-300 nm.

3. A method according to claim 1 including subjecting the sample between assessments to UV radiation in a wavelength range 250-260 nm.

4. A method according to claim 1 including subjecting the sample between assessments to UV radiation of about 254 nm wavelength.

5. A method according to claim 1 including subjecting the sample to UV radiation between assessments for less than 5 minutes.

6. A method according to claim 1 including measuring actual fluorescence of the sample in said assessment steps.

7. A method according to claim 6 including measuring any change in actual fluorescence between the assessment and the reassessment steps.

8. A method according to claim 1 comprising assessing and reassessing the fluorescence of the sample by reference to substantially only horizontally polarised fluorescent light.

9. A method according to claim 8 including causing the fluorescence to pass a filter oriented to pass substantially only horizontally polarised light.

10. A method according to claim 9 including in the assessment and reassessment steps exposing the sample to vertically polarised light as excitation light.

11. A method according to claim 1 including spectrally resolving the fluorescence observed in the assessment and reassessment steps.

12. A method according to claim 11 including spectrally resolving the fluorescence observed in the assessment and reassessment steps and analysing a shape of the fluorescence.

13. A method according to claim 1 including assessing the fluorescence of the sample, subjecting the sample to a pulse of UV radiation, and reassessing the fluorescence of the sample after a delay.

14. A method according to claim 13 including reassessing the fluorescence of the sample after a period of time substantially corresponding to a fluorescence lifetime of a class of glycated proteins or peptides.

15. A method according to claim 1 including assessing the fluorescence of the sample, subjecting the sample to a modulated UV signal, and reassessing the fluorescence of the sample for a modulated response.

16. A method according to claim 1 wherein the sample is a portion of skin of a living person or animal or a sample from a living person or animal.

17. A method according to claim 1 wherein the sample is of or from a person and including assessing the sample for the presence of glycated proteins or peptides as indicative of the presence of a disease in the person.

18. A method according to claim 17 wherein the disease is selected from any one or more of retinal dysfunction, cardiovascular disease, obesity, metabolic syndrome, diabetes, neurodegenerative disease, cancer, and renal disease.

19. A method according to claim 18 wherein the disease is diabetes.

20. A method of diagnosing diabetes in a person or a likelihood of a person becoming diabetic, which comprises steps of first assessing the skin or a blood sample of the person for fluorescence, subjecting the skin or blood sample to UV radiation, and reassessing the skin or blood sample for an increase in fluorescence relative to any fluorescence assessed in said first assessing step, the presence of fluorescence at said first assessing step and an increase in fluorescence at said reassessing step being indicative of the presence of diabetes or likelihood of the person becoming diabetic.

* * * * *